(12) United States Patent
Arvidson et al.

(10) Patent No.: US 8,164,756 B2
(45) Date of Patent: Apr. 24, 2012

(54) SYSTEM AND METHOD OF FLUID EXPOSURE AND DATA ACQUISITION

(75) Inventors: Rolf S. Arvidson, Sugar Land, TX (US); Andreas Luttge, Katy, TX (US)

(73) Assignee: William Marsh Rice University, Houston, TX (US)

( * ) Notice: Subject to any disclaimer, the term of this patent is extended or adjusted under 35 U.S.C. 154(b) by 371 days.

(21) Appl. No.: 12/569,443

(22) Filed: Sep. 29, 2009

(65) Prior Publication Data

US 2010/0079763 A1    Apr. 1, 2010

Related U.S. Application Data

(60) Provisional application No. 61/101,090, filed on Sep. 29, 2008.

(51) Int. Cl.
*G02B 9/02* (2006.01)
*G01N 1/10* (2006.01)
(52) U.S. Cl. ........................ 356/450; 356/246
(58) Field of Classification Search .............. 356/246, 356/450
See application file for complete search history.

(56) References Cited

U.S. PATENT DOCUMENTS

| | | | | |
|---|---|---|---|---|
| 5,991,697 | A * | 11/1999 | Nelson et al. | 702/49 |
| 7,324,215 | B2 * | 1/2008 | Luttge et al. | 356/512 |
| 7,373,259 | B2 * | 5/2008 | Lustig et al. | 702/31 |
| 7,749,442 | B2 * | 7/2010 | Koike et al. | 422/68.1 |
| 2011/0032511 | A1 * | 2/2011 | Luttge et al. | 356/35.5 |

OTHER PUBLICATIONS

Jardim, D. Faragó, et al., "Observing bacterial activity interferometrically," Eur Biophys J, 2003, pp. 159-162, vol. 32, EBSA.
Machado, R. R. P., et al., "Metabolic activity interferometer: description and calibration of an interferometric method to measure growth of mycobacteria," Eur Biophys J, 2008, pp. 111-119, vol. 38, European Biophysical Societies' Association.
Nagashima, Kazushige, et al., "Solute distribution in front of an ice/water interface during directional growth of ice crystals and its relationship to interfacial patterns," J. Phys. Chem. B, 1997, pp. 6174-6176, vol. 101, No. 32, American Chemical Society.
Reed, Jason, et al., "Live cell interferometry reveals cellular dynamism during force propagation," www.acsnano.org, 2008, pp. 841-846, vol. 2, No. 5, American Chemical Society. Snaked, Natan T., et al., "Reflective interferometric chamber for quantitative phase imaging of biological sample dynamics," Journal of Biomedical Optics, May/Jun. 2010, pp. 030503-1 to 030503-3, vol. 15, No. 3, SPIE.
Tsukamoto, Katsuo, et al., "Developments in interferometric techniques for in-situ observation of surface kinetics of crystals in solutions and three-dimensional analysis of transport phenomena," 2010, pp. 292-315 plus 1 cover page, American Institute of Physics.
Tsukamoto, Katsuo, et al., "Interferometric techniques for investigating growth and dissolution of crystals in solutions," 2007, pp. 329-341 plus 1 cover page, American Institute of Physics.

* cited by examiner

*Primary Examiner* — Michael A Lyons
(74) *Attorney, Agent, or Firm* — Conley Rose, P.C.; Rodney B. Carroll

(57) ABSTRACT

An apparatus has a data acquisition device, an environmental cell in a spatial registration relative to the data acquisition device, the environmental cell being configured to support a sample, and a fluid management system configured to initiate and discontinue exposure of the sample to a reaction fluid while the spatial registration is maintained. A method of performing data acquisition for a sample includes spatially registering the sample relative to a data acquisition device, at least partially exposing the sample to a reaction fluid while substantially maintaining the spatial registration of the sample relative to the data acquisition device, at least partially discontinuing exposing the sample to the reaction fluid while substantially maintaining the spatial registration of the sample relative to the data acquisition device, and acquiring data about the sample while substantially maintaining the spatial registration of the sample relative to the data acquisition device.

20 Claims, 4 Drawing Sheets

SYSTEM AND METHOD OF FLUID EXPOSURE AND DATA ACQUISITION

CROSS-REFERENCE TO RELATED APPLICATIONS

The present application claims priority to U.S. Provisional Patent Application 61/101,090 filed Sep. 29, 2008 by Rolf S. Arvidson, et al. and entitled "Environmental Fluid Flow Cell for Vertical Scanning Interferometer," which is incorporated herein by reference as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

It is sometimes desirable to investigate the effects of exposing a sample to a reaction fluid over time. In some systems, a sample may be exposed to a reaction fluid in a first device but must thereafter be transferred from the first device to a data acquisition device to perform the data acquisition. In such systems, the period of time during which the sample is not either exposed to the reaction fluid or maintained in a controlled environment may degrade and/or invalidate the results of the investigation. Accordingly, reducing the time during which a sample is removed from a reaction fluid for the purpose of performing data acquisition may be desirable.

SUMMARY

In some embodiments of the disclosure, an apparatus comprises a data acquisition device, an environmental cell in a spatial registration relative to the data acquisition device, the environmental cell being configured to support a sample, and a fluid management system configured to initiate and discontinue exposure of the sample to a reaction fluid while the spatial registration is maintained.

In some embodiments of the disclosure, a method of performing data acquisition for a sample is provided. The method may comprise spatially registering the sample relative to a data acquisition device, at least partially exposing the sample to a reaction fluid while substantially maintaining the spatial registration of the sample relative to the data acquisition device, at least partially discontinuing exposing the sample to the reaction fluid while substantially maintaining the spatial registration of the sample relative to the data acquisition device, and acquiring data about the sample while substantially maintaining the spatial registration of the sample relative to the data acquisition device.

In some embodiments of the disclosure, an apparatus comprising an interferometer having an optical objective and an environmental cell spatially registered relative to the interferometer is provided. The apparatus further comprises a fluid supply component configured to selectively supply a reaction fluid to the environmental cell, a fluid evacuation component configured to selectively evacuate substantially all of the reaction fluid from the environmental cell, and a scavenger tube configured to limit at least one of a dimension and a volume of a fluid envelope formed by the reaction fluid supplied to the environmental cell.

These and other features will be more clearly understood from the following detailed description taken in conjunction with the accompanying drawings and claims.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

Disclosed herein are systems and methods for controlling the exposure of samples to fluids and thereafter acquiring data about the sample. The systems and methods disclosed herein may be configured and/or implemented to expose a sample to fluids for a selected period of time and, after the exposure of the sample to the fluids is substantially discontinued, to acquire data about the sample. Accordingly, some systems disclosed herein may be referred to as Fluid Exposure and Data Acquisition (FEDA) systems.

Figure 1:
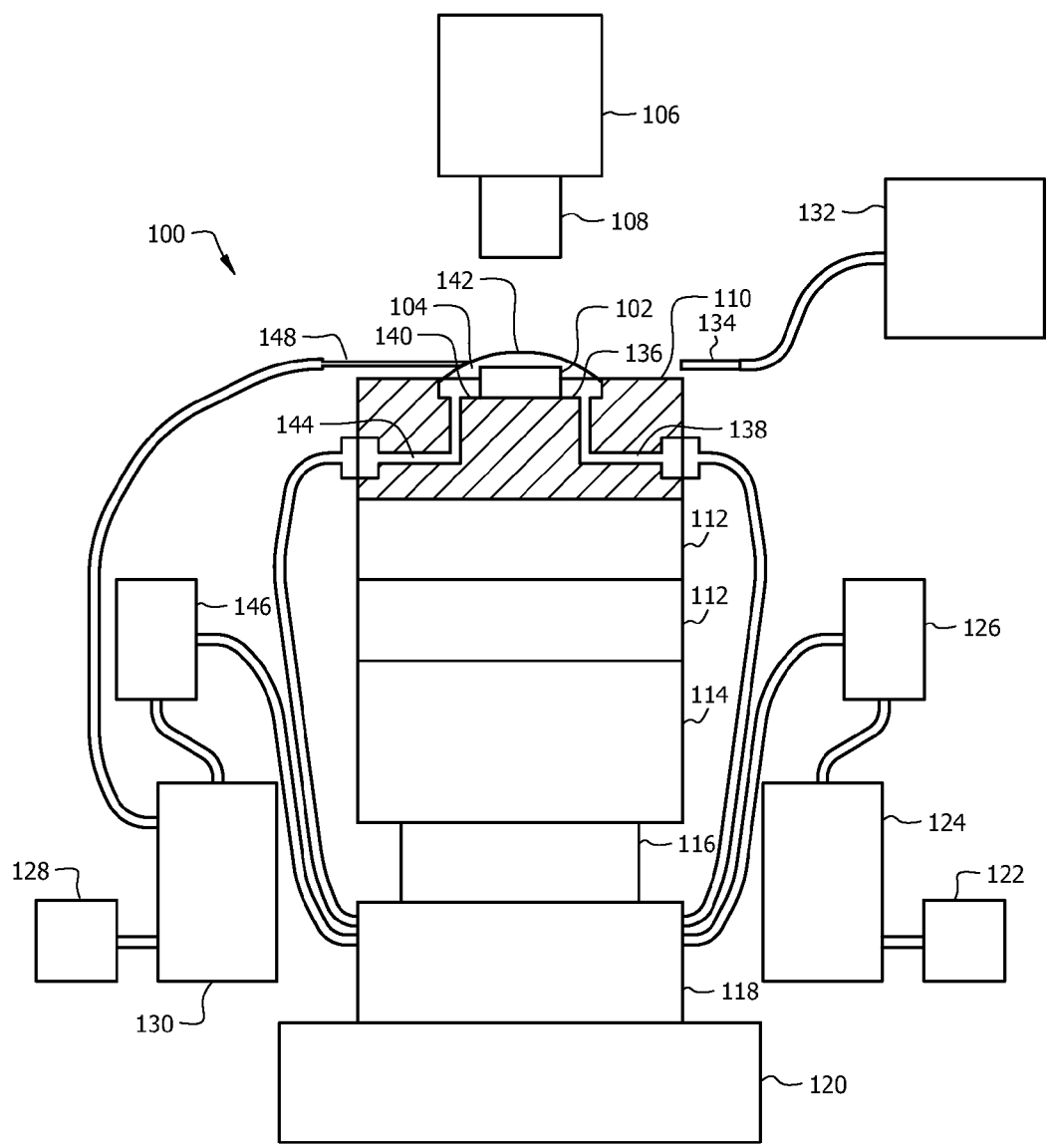
FIG. 1 is a simplified schematic view of an embodiment of a Fluid Exposure and Data Acquisition system of the disclosure.

FIG. 1 is a simplified schematic view of a FEDA system 100 according to an embodiment of the disclosure. The FEDA system 100 is generally configured to selectively expose a sample 102 to a reaction fluid 104 and is also configured to acquire data about the sample 102. In this embodiment, the FEDA system 100 is configured to allow repeated exposures of the sample 102 to the reaction fluid 104 and to acquire data about the sample (perform data acquisition) at times when the sample 102 is not substantially exposed to the reaction fluid 104. The FEDA system 100 may be configured to perform an initial data acquisition prior to exposing the sample 102 to the reaction fluid 104. As further explained below, the FEDA system 100 may also be configured to perform data acquisition after an initial exposure of the sample 102 to the reaction fluid 104 is discontinued and/or may be configured to perform data acquisition between discrete periods of exposure of the sample 102 to the reaction fluid 104.

The FEDA system 100 generally comprises a data acquisition device (DAD) 106 for obtaining data about the sample 102. In this embodiment, the DAD 106 may be a vertical scanning interferometer comprising an optical objective 108. In other embodiments, the DAD 106 may comprise any other suitable data acquisition device, such as, but not limited to, other types of interferometers, atomic force microscopes, cameras, probes, and/or other non-destructive evaluation tools (such as x-ray devices, ultrasonic wave devices, thermal imaging devices, electrical resistance meters, radiation emission detection devices, spectrometers, spectroscopes, and/or other spectroscopic instruments). Further, in other embodiments, the DAD 106 may comprise destructive evaluation tools, such as, but not limited to, cutters, cleaners, surface finishers, and/or other tools that acquire data by at least partially disturbing the physical structure and/or chemical makeup of the sample 102.

The FEDA system 100 further comprises components for supporting the sample 102 within the focal range of the DAD 106. Of course, considering the relatively high resolution of the DAD 106, the FEDA system 100 comprises components for establishing and maintaining a relatively precise spatial registration between the sample 102 and the DAD 106. More specifically, the sample 102 may be supported by an environmental cell 110. In this embodiment, the environmental cell 110 may be a substantially block-shaped structure formed from Plexiglas®. However, in alternative embodiments, the environmental cell 110 may be formed from any other suitable material that is generally inert with respect to the sample 102 or that generally reacts with the sample 102 in a substantially predictable manner. Further details of the shape and additional functional purposes of the environmental cell 110 are discussed below. Maintaining the spatial registration between the sample 102 and the DAD 106 is further accomplished through the use of one or more spatial registration and/or mechanical isolation devices, for example but not limited to, Tip-Tilt stages 112, Multi-Axis stages 114, wafer-based vibration isolation devices 116, liquid flow vibration reducers 118, anti-vibration controllers 120, and/or optics tables. In this embodiment, the various spatial registration and/or mechanical isolation devices may be manually controlled and/or computer controlled to establish and/or maintain the above-mentioned relative spatial registration between the sample 102 and the DAD 106 within a few nanometers or less.

The FEDA system 100 further comprises fluid control components configured to allow control over the fluids to which sample 102 is exposed. More specifically, a reaction fluid pump 122 is operable to pump reaction fluid 104 from a reaction fluid supply 124 into contact with the sample 102. Flow of the reaction fluid 104 from the reaction fluid supply 124 may be controlled by reaction fluid supply valve 126. Further, a vacuum pump 128 is operable to draw reaction fluid 104 from the vicinity of the sample 102 into a reaction fluid receiver 130. In this embodiment, reaction fluid 104 may be drawn into the reaction fluid receiver 130 through two routes, each of which are discussed in greater detail below. Still further, a gas supply 132 is operable to selectively supply a flow of gas from a gas nozzle 134 and into the vicinity of sample 102 as described in greater detail below. The gas provided by gas supply 132 may comprise a single gas or a mixture of gasses. Alternatively, gas supply 132 may be configured to provide any other composition of fluids of fixed composition, known composition, and/or at least partially determinable composition. In some embodiments, the gas provided by gas supply 132 may comprise oxygen to promote an aerobic environment adjacent the sample 102. However, in other embodiments, inert gasses such as nitrogen, argon, and/or other inert gasses may be supplied by gas supply 132 to promote an anaerobic and/or anoxic environment adjacent the sample 102. It will be appreciated that the gas supply 132 may be configured to supply any selected fluid and/or fluid mixture suitable for reducing direct and/or arbitrary contact with the otherwise ambient atmosphere of the relative laboratory.

To show the structure of the environmental cell 110 with greater clarity, the environmental cell 110 of FIG. 1 is shown in cross-section. In this embodiment, the environmental cell 110 comprises a concavity 136 into which the sample 102 may be received. While the concavity 136 is shown as being a substantially cylindrical depression and/or recess, in other embodiments, the concavity 136 may be a generally spherical section shaped depression and/or recess or any other suitably shaped concavity 136. Further, the environmental cell 110 comprises an integral delivery channel 138 through which reaction fluid 104 may be pumped and introduced into the concavity 136. In this embodiment, the integral delivery channel 138 extends from a side of the environmental cell 110, through the interior of the environment cell 110, and to an opening in a floor of the concavity 136. After a sufficient amount of reaction fluid 104 is introduced to the concavity 136, the reaction fluid 104 may at least partially envelop the sample 102, thereby exposing the sample 102 to the reaction fluid 104. As shown in FIG. 1, the reaction fluid 104 may be provided in such volume that substantially the entire sample 102 is within a reaction fluid envelope 140, the outermost boundary of such fluid envelope 140 being bound by a reaction fluid interface 142 that is not bound by other structures. In this embodiment, the fluid envelope 140 may be bound by the above-mentioned reaction fluid interface 142 and the walls of the concavity 136.

The environmental cell 110 further comprises an integral evacuation channel 144 that extends from a side of the environmental cell 110, through the interior of the environment cell 110, and to an opening in a floor of the concavity 136. The integral evacuation channel 144 provides a path through which reaction fluid 104 may travel to the reaction fluid receiver 130 when the evacuation valve 146 is open. Reaction fluid 104 may also travel from the vicinity of the sample 102 to the reaction fluid receiver 130 through a scavenger tube 148. The scavenger tube 148 is a needle-like tube through which vacuum pressure is applied to draw reaction fluid 104 out of the fluid envelope 140 due to the scavenger tube 148 being located adjacent the reaction fluid interface 142. The spatial location of the scavenger tube 148, in some embodiments, may determine a height of the fluid envelope 140 and/or a diameter of the fluid envelope 140, consequently determining a volume of the fluid envelope 140.

In operation, the FEDA system 100 may be used to repeatedly expose the sample 102 to the reaction fluid 104. In between those exposures, the DAD 106 may be used to acquire data about the sample 102. More specifically, the FEDA system 100 may be used to expose the sample 102 to reaction fluid 104, discontinue exposing the sample 102 to the reaction fluid 104 by removing and or reducing the size of the fluid envelope 140, perform data acquisition, and optionally repeat the fluid exposure and subsequent data acquisition. In that manner, a series of data sets may be acquired by the DAD 106 that show the time progressive effects of exposing the sample 102 to the reaction fluid 104.

The FEDA system 100 may be initially configured by placing the sample 102 on the environmental cell 110. Next, the sample 102 may be spatially registered with respected to the DAD 106 and/or objective 108 by adjusting and/or activating one or more of the spatial registration and/or mechanical isolation devices, namely, Tip-Tilt stages 112, Multi-Axis stages 114, wafer-based vibration isolation devices 116, liquid flow vibration reducers 118, anti-vibration controllers 120, and/or optics tables. Once the sample 102 is spatially registered with respect to the DAD 106 and/or objective 108, the reaction fluid pump 122 and the vacuum pump 128 may be started. The reaction fluid pump 122 may be a damped peristaltic pump or a high capacity syringe pump, both types being well suited for providing a substantially constant reaction fluid 104 flow rate. The vacuum pump 128 may be operated so that the scavenger tube 148 and/or the integral evacuation channel 144 may remove reaction fluid 104 from the fluid envelope 140 and/or concavity 136 at a much higher rate than the reaction fluid 104 is provided by the reaction fluid pump 122.

Prior to exposing the sample 102 to any reaction fluid 104, the DAD 106 may be used to acquire data about the sample 102. Next, the reaction fluid supply valve 126 may be opened and/or otherwise operated to allow flow of reaction fluid 104 from the reaction fluid supply 124 to the liquid flow vibration reducer 118. From the liquid flow vibration reducer 118, the reaction fluid 104 may flow to the concavity 136 through the integral delivery channel 138. During such transfer of reaction fluid 104 to the concavity 136, the evacuation valve 146 remains closed or is otherwise operated to prevent drawing reaction fluid 104 away from the concavity 136 through the integral evacuation channel 144. However, the scavenger tube 148 is operated during the transfer of reaction fluid 104 to the concavity 136. The location of the scavenger tube 148 may be such that operation of the scavenger tube 148 allows the fluid envelope 140 to grow and/or enlarge until the reaction fluid interface 142 contacts the scavenger tube 148. Upon contact with the scavenger tube 148, reaction fluid 104 may be drawn from the fluid envelope 140 in a manner that limits the size (height and/or diameter) of the fluid envelope 140, thereby limiting the volume of the fluid envelope 140. In some embodiments, a substantially constant flow of reaction fluid 104 may be provided to the concavity 136. In such cases, even though additional reaction fluid 104 is supplied to the concavity 136, the fluid envelope 140 may be maintained at a substantially constant size and/or volume because of the above mentioned fluid scavenging performed by the scavenger tube 148. In this way, the fluid envelope 140 may be controlled to envelop the sample 102 in a desired manner.

After exposing the sample 102 to the above-described substantially constant fluid flow for a desired and/or preset amount of time, the supply fluid flow may be stopped by closing the reaction fluid supply valve 126. In some embodiments, evacuation of reaction fluid 104 from the concavity 136 may begin at substantially the same time reaction fluid 104 supply to the concavity 136 is discontinued. Evacuation of reaction fluid 104 from the concavity 136 may be performed by opening the evacuation valve 146, allowing the vacuum pressure generated by vacuum pump 128 to draw the reaction fluid 104 to the liquid flow vibration reducer 118 through the integral evacuation channel 144. The reaction fluid 104 may then flow from the liquid flow vibration reducer 118 to the reaction fluid receiver 130. During the evacuation of the reaction fluid 104, the gas supply 132 may supply a flow of gas from a gas nozzle 134 and into the vicinity of sample 102 to help dry off or otherwise remove reaction fluid 104 from the sample 102. The reaction fluid 104 blown off the sample 102 may evaporate and/or may be evacuated through the integral evacuation channel 144.

Next, the DAD 106 may be operated to obtain data about the sample 102. During the data acquisition, gas may continue to be supplied by the gas nozzle 134 into the vicinity of sample 102 to reduce and/or displace other ambient gasses (such as air and/or oxygen) so that the sample 102 is selectively exposed primarily to the gas while the sample 102 is not within the fluid envelope 140. After the data acquisition, exposure of the sample 102 to reaction fluid 104 may again be established by closing the evacuation valve 146 and opening the reaction fluid supply valve 126 to deliver reaction fluid 104 to the concavity 136, once again resulting in the existence of a fluid envelope 140. In some embodiments, the processes of evacuating the reaction fluid 104 from the concavity 136, drying the sample 102 using the gas, acquiring data about the sample 102, and reestablishing the fluid envelope 140 around the sample 102 may take a combined time of about 10-30 seconds. It will be appreciated that the 10-30 seconds may represent a very small amount of time as compared to the amount of time the sample 102 is exposed to the reaction fluid 104. Further, because the timing of the application, evacuation, and reapplication of reaction fluid 104 is known precisely in the above-described embodiments, the tracking and/or computation of the actual amount of time a sample 102 is exposed to the reaction fluid 104 (e.g., the amount of time the sample 102 is wetted or non-wetted with the reaction fluid 104) is easily incorporated into analysis of data acquired.

Figure 2:
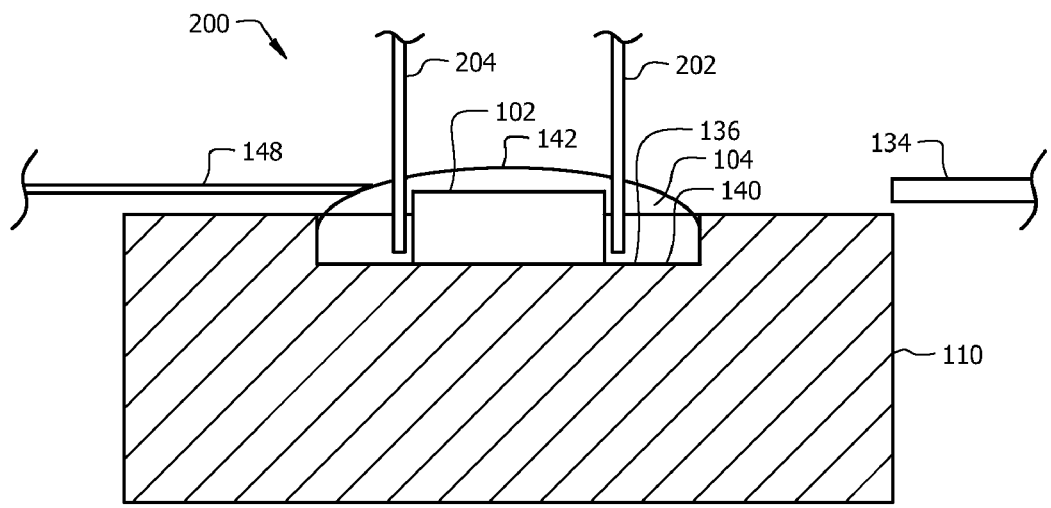
FIG. 2 is a simplified schematic view of another embodiment of a Fluid Exposure and Data Acquisition system of the disclosure.

Referring now to FIG. 2, an alternative embodiment of a FEDA system 200 is shown. FEDA system 200 is substantially similar to FEDA system 100 but with two primary differences. In this embodiment, environmental cell 110 does not comprise an integral delivery channel 138 or an integral evacuation channel 144. Instead of providing fluid to the concavity 136 through the integral delivery channel 138, the FEDA system 200 comprises a fluid supply tube 202 that may be lowered into the concavity 136 to deliver reaction fluid 104 to form the fluid envelope 140. Similarly, instead of evacuating fluid from the concavity 136 through the integral evacuation channel 144, the FEDA system 200 comprises a fluid evacuation tube 204 that may be lowered into the concavity 136 to evacuate reaction fluid 104. The tubes 202, 204 generally provide the same fluid delivery and fluid evacuation as their channel 138, 144 counterparts but with an added benefit of further mechanically decoupling the fluid control components from the environmental cell 110. Since the FEDA system 200 does not mechanically couple the tubes 202, 204 to the environmental cell 110, vibration and/or movement of the tubes 202, 204 is not transferred to the environmental cell 110, thereby promoting enhanced maintenance of spatial registration between the DAD 106 and the sample 102.

Figure 3:
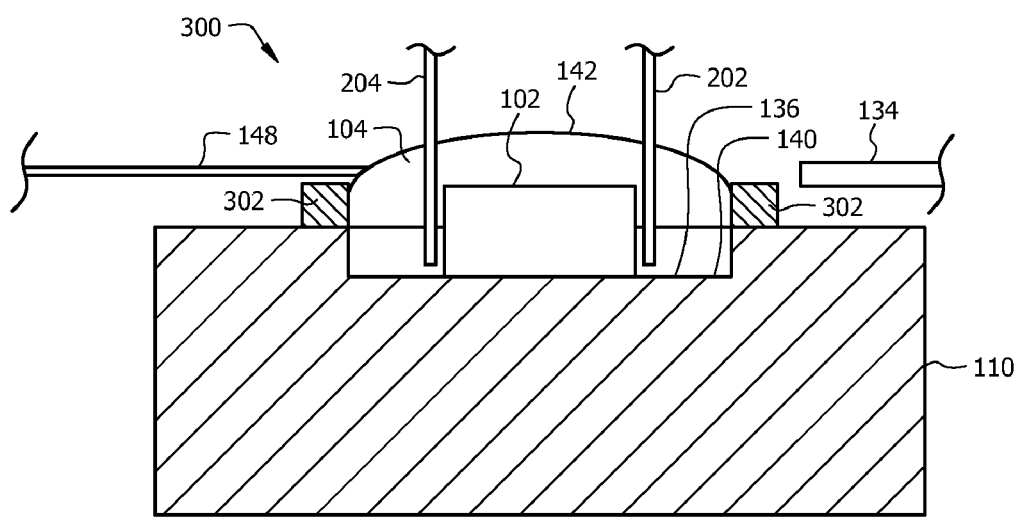
FIG. 3 is a simplified schematic view of yet another embodiment of a Fluid Exposure and Data Acquisition system of the disclosure.

Referring now to FIG. 3, an alternative embodiment of a FEDA system 300 is shown. FEDA system 300 is substantially similar to FEDA system 200 but with the addition of an o-ring 302 attached to the environmental cell 110. Attachment of the o-ring 302 allows the fluid envelope 140 to grow taller and more easily accommodate a taller sample 102 that may protrude significantly beyond the upper surface of the environmental cell 110.

Figure 4:
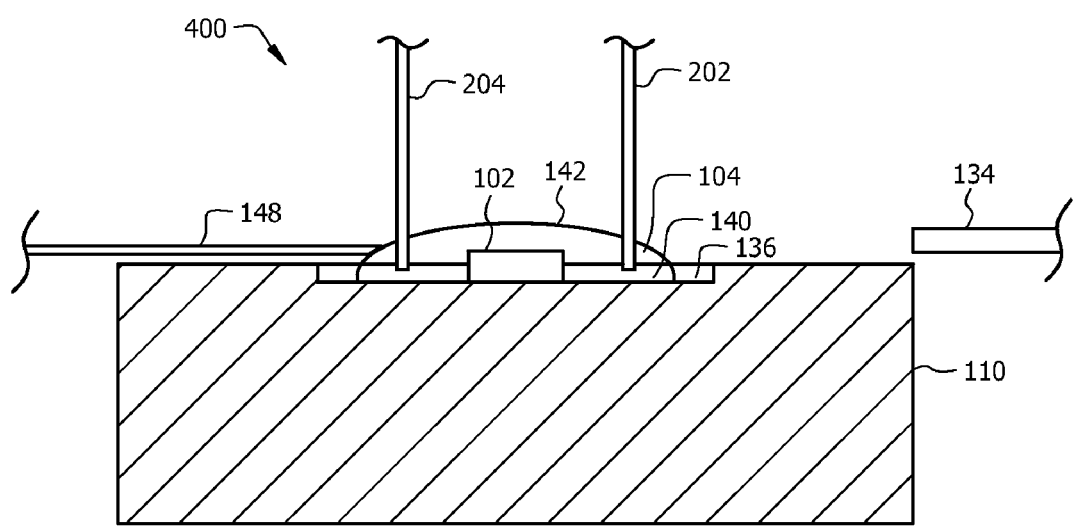
FIG. 4 is a simplified schematic view of still another embodiment of a Fluid Exposure and Data Acquisition system of the disclosure.

Referring now to FIG. 4, an alternative embodiment of a FEDA system 400 is shown. FEDA system 400 is substantially similar to FEDA system 200 but with the concavity 136 being sized and shaped relative to the size and shape of the sample 102 so that the fluid envelope 140 is not defined by the sidewalls of the concavity 136. This configuration shows that, in some embodiments, reaction fluid 104 delivered to the concavity 136 may envelop the sample 102 in a manner in which the reaction fluid interface 142 generally extends around the sample and interfaces only the floor of the concavity 136. It will be appreciated that relatively shallow and/or relatively large diameter concavities 136 may produce such a fluid envelope 140 that resembles a bubble and/or a droplet.

It will be appreciated that some of the FEDA systems 100, 200, 300, 400 disclosed herein allow for near in situ data acquisition without the need to immerse the objective 108 in the reaction fluid, without the need to correct for data acquisition noise and/or differences due to data acquisition through a liquid, and without the need to disturb the spatial registration of the sample 102 with respect to the DAD 106. By simply draining and/or evacuating the reaction fluid for a short amount of time, data acquisitions may be made before detrimental desiccation and/or detrimental exposure to gases such as air and/or oxygen limit or invalidate the data acquisitions in some way. Further, in embodiments where the DAD 106 is an interferometer, the FEDA systems 100, 200, 300, 400 disclosed each allow for long term analysis of the same physical area of a sample 102 surface without the need to re-register the sample 102 relative to the DAD 106. The systems and methods disclosed herein may be applied to samples of many types, including but not limited to, life sciences samples (microbiologic, enzyme, bacterial), minerals, glasses, and metals. It will be appreciated that where the above discussion refers to spatially registering a sample 102 relative to a DAD 106, the same type of registration may be performed with the environmental cell 110 relative to the DAD 106, providing substantially similar results in spatial registration and registration maintenance. Further, it will be appreciated one or more of the components of the FEDA systems 100, 200, 300, 400 that control the exposure of the sample 102 to the reaction fluid 104 may be referred to as components of a fluid management system.

In other embodiments, the systems and methods disclosed herein may be configured and/or implemented to continue controlled exposure of a sample 102 to reaction fluids 104 even while acquiring data about the sample 102. For example, a sample 102 may be exposed to reaction fluids 104 so that a fluid envelope 140 having selected dimensions may remain in contact with the sample 102 while using the DAD 106 to acquire data about the sample 102. It will be appreciated that a flow or volume of fluid 104 may be manipulated in a manner that provides a fluid envelope 140 of a selected height/thickness, diameter, and/or fluid flow rate therethrough. In such embodiments, the DAD 106 may be adjusted, compensated, and/or otherwise configured to acquire data about sample 102 in spite of the presence of a fluid envelope 140 in contact with the sample 102.

In some embodiments, a fluid envelope 140 may be maintained to comprise a selected thickness and/or height above sample 102 and the DAD 106 and/or an objective 108 of the DAD 106 may be configured to be operated in a mode compatible with investigating and/or observing the sample 102 through a selected and/or known combination of fluids. More specifically, the DAD 106 may be configured to successfully acquire data about sample 102 even where reaction fluid 104 is present in a light path of the objective 108 of the DAD 106. It will be appreciated that the embodiments disclosed herein provide for controlling flows of fluids such as reaction fluid 104 and fluids and/or gas emitted from gas supply 132 and for use of compatibly configured DADs 106 to acquire data about the samples 102. The samples 102 may be exposed to fluids in a variety of controlled manners and the DADs 106 may be used to acquire data about the samples 102 prior to, during, subsequent, and/or between such exposures.

EXAMPLES

Example 1

Figure 5:
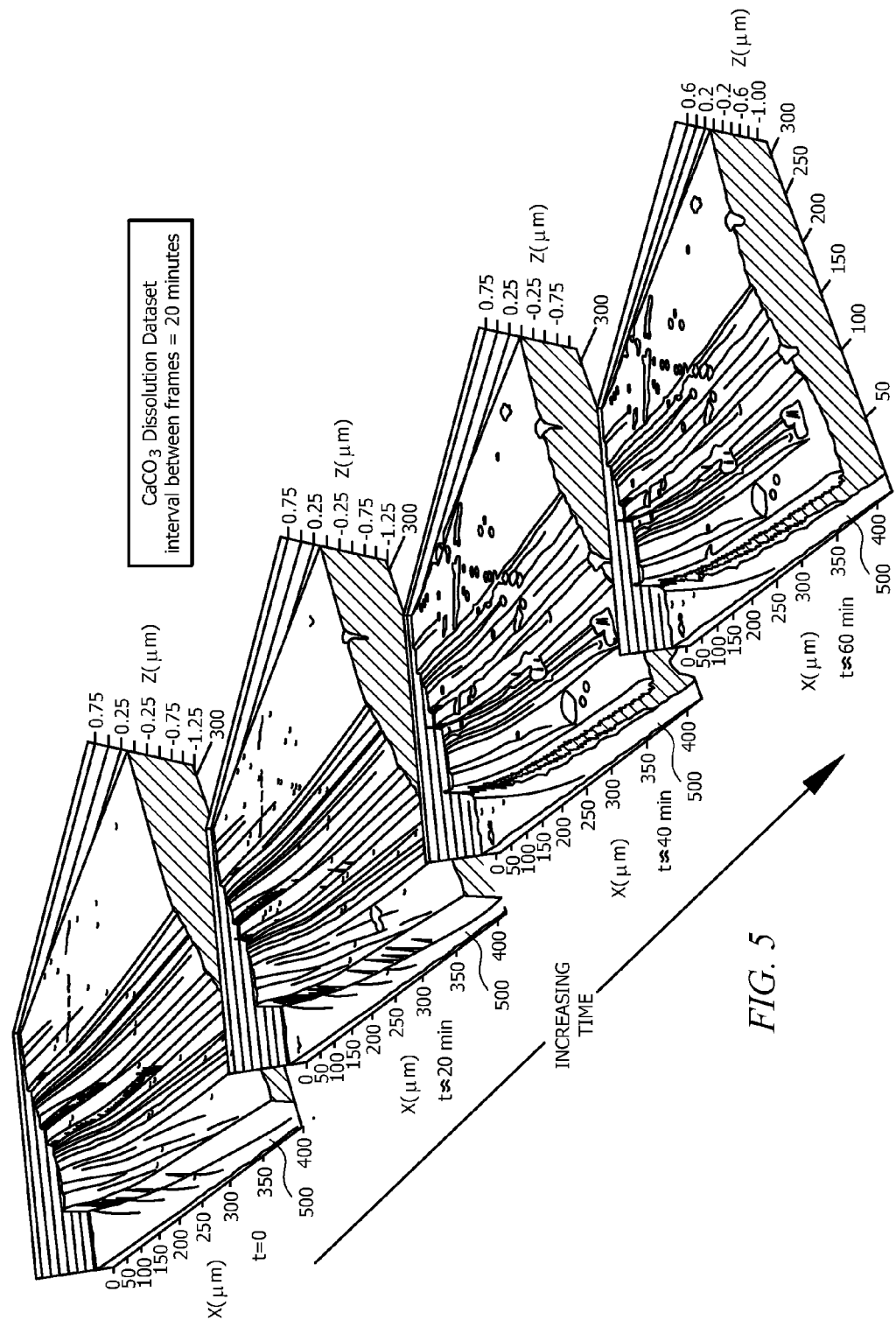
FIG. 5 is a series of rendered data sets as actually obtained by a Fluid Exposure and Data Acquisition system of the disclosure.

Referring now to FIG. 5, a series of rendered data sets representative of a sample surface obtained by a FEDA system substantially similar to FEDA system 100 is shown. In this example, the first rendered data set represents the sample 102 surface at time=0, prior to exposing the sample 102 surface to a reaction fluid 104. The second rendered data set represents the sample 102 surface after about 20 minutes of exposure to reaction fluid 104. The third rendered data set represents the sample 102 surface after a total of about 40 minutes of exposure to reaction fluid 104. The fourth rendered data set represents the sample 102 surface after a total of about 60 minutes of exposure to reaction fluid 104. In this example, about 10-30 seconds elapsed between each set of 20 minute exposures of the sample 102 to the reaction fluid 104. During the 10-30 second periods of time, the reaction fluid 104 was evacuated form the concavity 136, the surface of the sample 102 was blown dry by the gas, the data was acquired, and the fluid envelope 140 was reestablished. This example further illustrates the technique of masking a reference plane 500 with a substance that is non-reactive with the reaction fluid 104 so that the data generated by the DAD 106 at the various time intervals may be compared against a common z-plane, providing easier comparative analysis of the rendered data sets. In this example, the sample 102 comprised calcium carbonate, the reaction fluid 104 comprised a sodium carbonate solution, and the gas was dry nitrogen.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure. The discussion of a reference in the disclosure is not an admission that it is prior art, especially any reference that has a publication date after the priority date of this application. The disclosure of all patents, patent applications, and publications cited in the disclosure are hereby incorporated by reference, to the extent that they provide exemplary, procedural, or other details supplementary to the disclosure.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

What is claimed is:

1. An apparatus, comprising:
   a data acquisition device;
   an environmental cell in a spatial registration relative to the data acquisition device, the environmental cell being configured to support a sample; and
   a fluid management system configured to initiate and discontinue exposure of the sample to a reaction fluid while the spatial registration is maintained.

2. The apparatus of claim 1, wherein the data acquisition device is a vertical scanning interferometer.

3. The apparatus of claim 1, wherein the environmental cell comprises a concavity for receiving at least a portion of the sample and for receiving at least a portion of the reaction fluid.

4. The apparatus of claim 3, wherein the environmental cell further comprises an integral channel in fluid communication with the concavity.

5. The apparatus of claim 3, wherein the concavity is substantially cylindrical in shape.

6. The apparatus of claim 1, wherein the fluid management system comprises a scavenger tube operable to limit at least one of a height and a diameter of a fluid envelope formed by the reaction fluid.

7. The apparatus of claim 6, wherein the scavenger tube removes reaction fluid from the fluid envelope in response to the scavenger tube contacting an interface of the reaction fluid.

8. A method of performing data acquisition for a sample, comprising:
   spatially registering the sample relative to a data acquisition device;
   at least partially exposing the sample to a reaction fluid while substantially maintaining the spatial registration of the sample relative to the data acquisition device;
   at least partially discontinuing exposing the sample to the reaction fluid while substantially maintaining the spatial registration of the sample relative to the data acquisition device; and
   acquiring data about the sample while substantially maintaining the spatial registration of the sample relative to the data acquisition device.

9. The method of claim 8, further comprising:
   flowing a gas near the sample to limit exposure of the sample to an ambient gas.

10. The method of claim 9, further comprising:
    creating and maintaining a fluid envelope during the at least partially exposing the sample to the reaction fluid; and
    limiting a dimension of the fluid envelope while flowing a substantially constant flow of the reaction fluid to the fluid envelope.

11. The method of claim 8, wherein the data acquisition device is a vertical scanning interferometer.

12. The method of claim 8, wherein the at least partially exposing the sample to a reaction fluid while substantially maintaining the spatial registration of the sample relative to the data acquisition device and the at least partially discontinuing exposing the sample to the reaction fluid while substantially maintaining the spatial registration of the sample relative to the data acquisition device are accomplished while mechanically isolating the sample from fluid transfer components.

13. The method of claim 8, further comprising:
    after acquiring the data about the sample, resuming at least partially exposing the sample to a reaction fluid while substantially maintaining the spatial registration of the sample relative to the data acquisition device;
    at least partially discontinuing exposing the sample to the reaction fluid while substantially maintaining the spatial registration of the sample relative to the data acquisition device; and
    acquiring additional data about the sample while substantially maintaining the spatial registration of the sample relative to the data acquisition device.

14. An apparatus, comprising:
    an interferometer having an optical objective;
    an environmental cell spatially registered relative to the interferometer;
    a fluid supply component configured to selectively supply a reaction fluid to the environmental cell;
    a fluid evacuation component configured to selectively evacuate substantially all of the reaction fluid from the environmental cell; and
    a scavenger tube configured to limit at least one of a dimension and a volume of a fluid envelope formed by the reaction fluid supplied to the environmental cell.

15. The apparatus of claim 14, wherein at least one of the fluid supply component and the fluid evacuation component are integral to the environmental cell.

16. The apparatus of claim 14, wherein the scavenger tube is configured to limit at least one of a height and a diameter of the fluid envelope by removing reaction fluid from the fluid envelope when the scavenger tube contacts an interface of the fluid envelope.

17. The apparatus of claim 14, wherein reaction fluid is supplied to the fluid envelope by the fluid supply component at substantially the same fluid flow rate as the fluid flow rate at which the scavenger tube removes fluid from the fluid envelope.

18. The apparatus of claim 14, wherein the environmental cell is actively maintained in the spatial registration with the interferometer.

19. The apparatus of claim 14, wherein the interferometer is a vertical scanning interferometer.

20. The apparatus of claim 14, wherein the environmental cell comprises a concavity configured to receive at least a portion of the sample and at least a portion of the reaction fluid.

* * * * *